United States Patent [19]
Adams et al.

[11] Patent Number: 5,366,487
[45] Date of Patent: Nov. 22, 1994

[54] FIBRILLATION AND TACHYCARDIA DETECTION

[75] Inventors: Theodore P. Adams, Edina; Mark W. Kroll, Minnetonka, both of Minn.

[73] Assignee: Angeion Corporation, Plymouth, Minn.

[21] Appl. No.: 147,464

[22] Filed: Nov. 4, 1993

Related U.S. Application Data

[63] Continuation of Ser. No. 848,147, Mar. 9, 1992, abandoned.

[51] Int. Cl.⁵ ............................................. A61N 1/00
[52] U.S. Cl. ......................................... 607/5; 128/705
[58] Field of Search ............... 128/695, 696, 700, 702, 128/705; 607/5, 6, 9, 14

[56] References Cited

U.S. PATENT DOCUMENTS

| | | | |
|---|---|---|---|
| 4,475,551 | 10/1984 | Langer et al. | 128/419 D |
| 4,750,494 | 6/1988 | King | 128/705 |
| 4,790,317 | 12/1988 | Davies | 128/419 |
| 4,799,493 | 1/1989 | DuFault | 128/419 D |
| 4,974,598 | 12/1990 | John | 128/696 |
| 5,010,887 | 4/1991 | Thornander | 128/696 |
| 5,193,550 | 3/1993 | Duffin | 128/702 |
| 5,199,438 | 4/1993 | Pearlman | 128/700 |

OTHER PUBLICATIONS

Mercando et al., "Measurement of Differences in Timing and Sequence Between Two Ventricular Electrodes as a Means of Tachycardia Differentiation", PACE, vol. 9, pp. 1069-1077.

Camm et al., "Tachycardia Recognition by Implantable Elecronic Devices", PACE, vol. 10, pp. 1175-1190.

Primary Examiner—Lee S. Cohen
Assistant Examiner—Marianne Parker
Attorney, Agent, or Firm—Patterson & Keough

[57] ABSTRACT

Providing a sensitive, prompt, and accurate indication of both ventricular fibrillation and monomorphic ventricular tachycardia is the aim of this invention. The invention employs electrical voltage-versus-time signals produced by the heart, these observed from two or more locations. By well-known signal-processing techniques, these signals are reduced to pulses of standardized height and duration, each derived from a prominent feature of the waveform for each heart period, such as its leading edge, in the process eliminating the irrelevant information in the waveform, but retaining the feature that is most relevant in the present context, namely, its precise time of occurrence. The invention then uses further standard electronic techniques to determine the amount of delay between the corresponding pulses in two such pulse trains, in the process distinguishing between monomorphic ventricular tachycardia and more benign conditions. It is a further straightforward matter of signal analysis to determine coincidence rate as a fraction of total pulse rate, which in the normal heart approaches unity (100%), while in the fibrillating heart is much lower, thus diagnosing ventricular fibrillation. The present invention is hence able to trigger a defibrillating-discharge decision, or a cardioversion-discharge in the prior case, much more reliably than has been possible in the prior art.

13 Claims, 8 Drawing Sheets

PULSE CORRELATION CONTROL

FIBRILLATION AND TACHYCARDIA DETECTION

This application is a file wrapper continuation of U.S patent application Ser. No. 07/848,147, filed Mar. 9, 1992, now abandoned.

BACKGROUND OF THE INVENTION

1. Field of the Invention

Implantable defibrillator cardioverter systems are the broad area that this invention concerns, with the specific focus being on methods for detecting the presence of ventricular fibrillation promptly and accurately, and for distinguishing fibrillation from tachycardias.

2. Description of the Prior Art

A major challenge in the defibrillation art is the prompt and accurate detection of the ventricular fibrillation condition. Fibrillation is the rapid, but unsynchronized, contraction of heart-muscle elements, causing the blood-pumping action of the heart to diminish seriously or even to cease. It clearly involves a departure from the pulse rate of normal sinus rhythm (NSR), 60 to 120 beats per minute, but is not unique in this respect because other and quite different conditions can also cause pulse-rate departures from NSR. The challenge thus is to define a reliable criterion for identifying the condition of ventricular fibrillation. Pulse rate alone is not a dependable criterion, even though it is often used for the purpose. Lacking a reliable criterion, there are the twin hazards of failing to detect the onset of fibrillation, and of applying a fibrillation shock when such treatment is not appropriate. The first of these lapses is fatal, and the second is painful and disconcerting, as well as potentially dangerous. Furthermore, the latter event represents a waste of precious and limited energy in the case of an implanted defibrillation system.

Conditions distinct from ventricular fibrillation that involve a rapid pulse, above 120 per minute, are identified by the generic term tachycardia. Further complicating the picture, however, is the fact that there are different kinds of tachycardia. Monomorphic ventricular tachycardia (MVT) involves degraded coordination in the contraction of the ventricle, but not the chaotic behavior found in fibrillation. It is a hazardous condition, and can be treated effectively in many cases by cardioversion, a shock with energy in the neighborhood of one joule, significantly less than is used in a typical defibrillation procedure.

Second, the condition of supraventricular tachycardia (SVT) involves better coordination than MVT and is usually not life-threatening. Since its origin is above the ventricular region, it does not respond to the most common cardioverter-defibrillator kinds of treatment that focus their energy delivery on the ventricular region. A type of SVT, known as sinus tachycardia, is caused by emotional or physical stress, and pumping action remains normally efficient so no intervention is necessary or desirable.

Thus, the diagnostic challenge is to distinguish among three conditions or sets of conditions: (1) Intervention is either not needed or not effective in the set comprising the conditions of normal sinus rhythm, sinus tachycardia, and supraventricular tachycardia. (2) A comparatively low-energy shock is appropriate in the case of monomorphic ventricular tachycardia. (3) A high-energy defibrillation shock is indicated in the case of ventricular fibrillation.

Electrical signals generated by the heart muscle are routinely sensed in pacemaker applications. Sometimes these signals are picked up by the pair of electrodes also used for delivering the pacing impulse. Normally these electrodes are near the distal end of a catheter that is introduced intravenously, and positioned at the right-ventricular apex. Typically, a tip electrode is right at the end of the catheter, and a ring electrode is positioned about one centimeter away from the end, as illustrated in FIG. 1.

Figure 1:
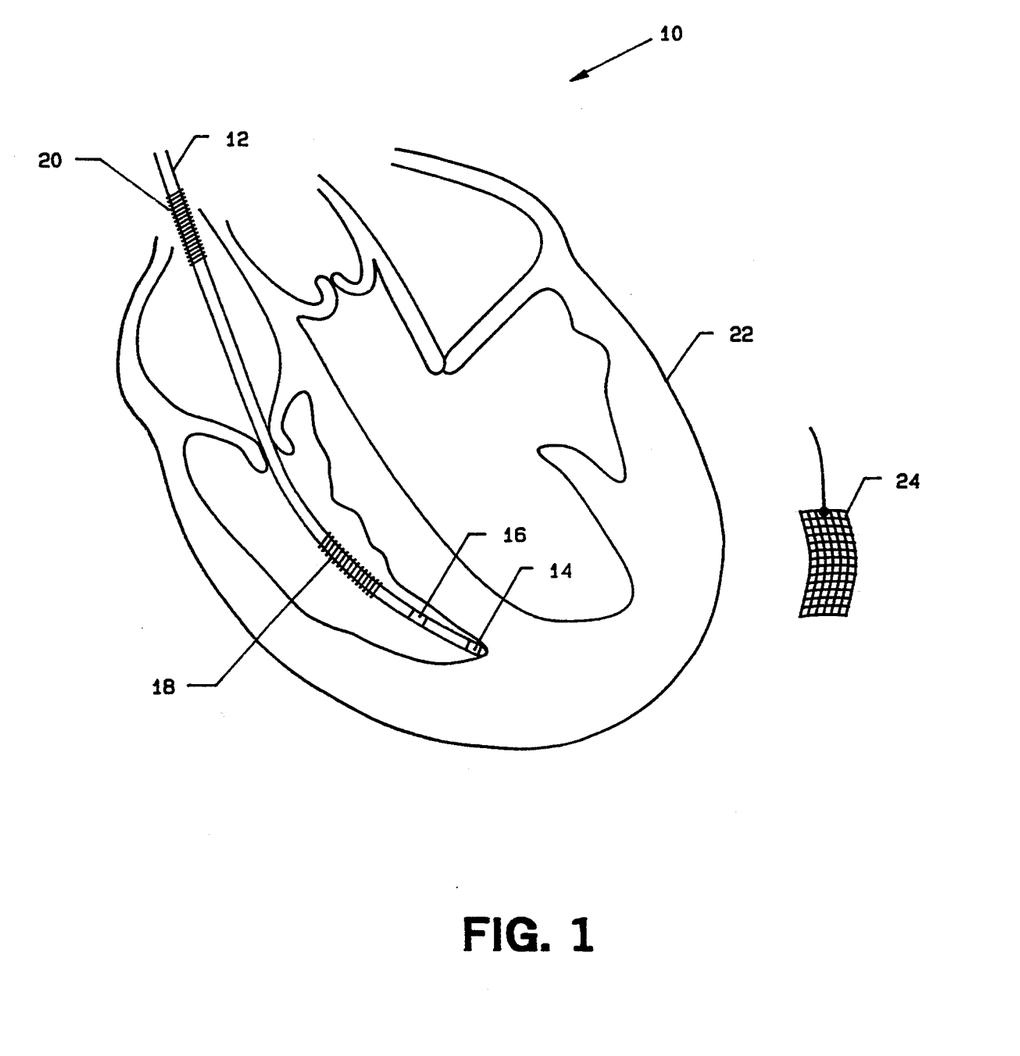
FIG. 1 illustrates schematically the heart with a pacemaker-defibrillator catheter inserted through the superior vena cava and into the right atrium and right ventricle, and also an associated subcutaneous-patch electrode.

Also shown schematically in FIG. 1 are two additional coils; electrodes associated with the catheter that are for delivering a defibrillation shock, one electrode located within the right ventricle, and one at the top of the right atrium. Another electrode option for defibrillation are the epicardial patches illustrated in FIG. 2. In either case, the defibrillation electrodes can also be used for picking up electrical heart-waveform signals, in lieu of or in addition to the two pacing electrodes. In still another arrangement, one of the defibrillation electrodes may serve as a common electrode for several purposes in addition to defibrillation—pacing, simple pulse detection, and waveform observation.

The shape, or morphology, of the electrical waveform delivered by the heart changes with the onset of fibrillation. But these changes, unfortunately, are neither consistent enough nor pronounced enough to serve as unsupported fibrillation criteria. One change is a tendency toward an erratic pulse (variable intervals between heartbeats), known commonly as a departure from rate stability. Another change is a tendency for heart voltage to be zero for a smaller fraction of the time, or a change in what is commonly described as the probability distribution function. That is, the signal dwells near the baseline for a smaller fraction of the cardiac period.

Because pulse observation is straightforward, a number of other features of simple pulse rate have been brought into use in an effort to improve the accuracy of fibrillation detection. Among these are rate acceleration, and time at a particular rate. But these indicators are equivocal, and consequently not even this elaborate method avoids "overlap" with the aggregate behavior of these pulse features in a heart functioning normally, or functioning in a manner such that a shock is not helpful. The monitoring of completely different variables, such as blood pH, pressure, and oxygen saturation are subjects of current research, but have not yet reached clinical application. Hence, the present invention seeks to exploit information already partly delivered by existing systems, but thus far unused.

SUMMARY OF THE INVENTION

The general purpose of the present invention is to provide a clearer and more reliable indication of the onset of ventricular fibrillation and monomorphic ventricular tachycardia than has been available in the prior art. A particular problem in prior art methods that employ the sensing of electrical signals generated by the heart muscle for this purpose is the local nature of the observation, which increases the tendency of a signal from a heart in fibrillation to appear quasinormal. Because the primary attribute of fibrillation is a lack of contraction coordination, or synchronism, in various parts of the heart, simultaneous observations at two or more sites will yield a clear advantage.

One element of the present invention, therefore, is the collecting and comparing of data from two or more information channels connected to the heart. This can be accomplished, for example, by using the two pairs of electrodes shown in FIG. 1, or the two pairs of electrodes in FIG. 2. In either case, these four electrodes can be reduced to three, with one serving as a common electrode. Even further advantage could be gained by going to three independent signals, derived, for example, from the pairs labeled B and C in FIG. 3 in addition to the pacing pair labeled A. Still another variation on the present invention would use one or more subcutaneous-patch electrodes, or else the housing of the defibrillator module, in concert with the kinds of electrodes already described.

Figure 4:
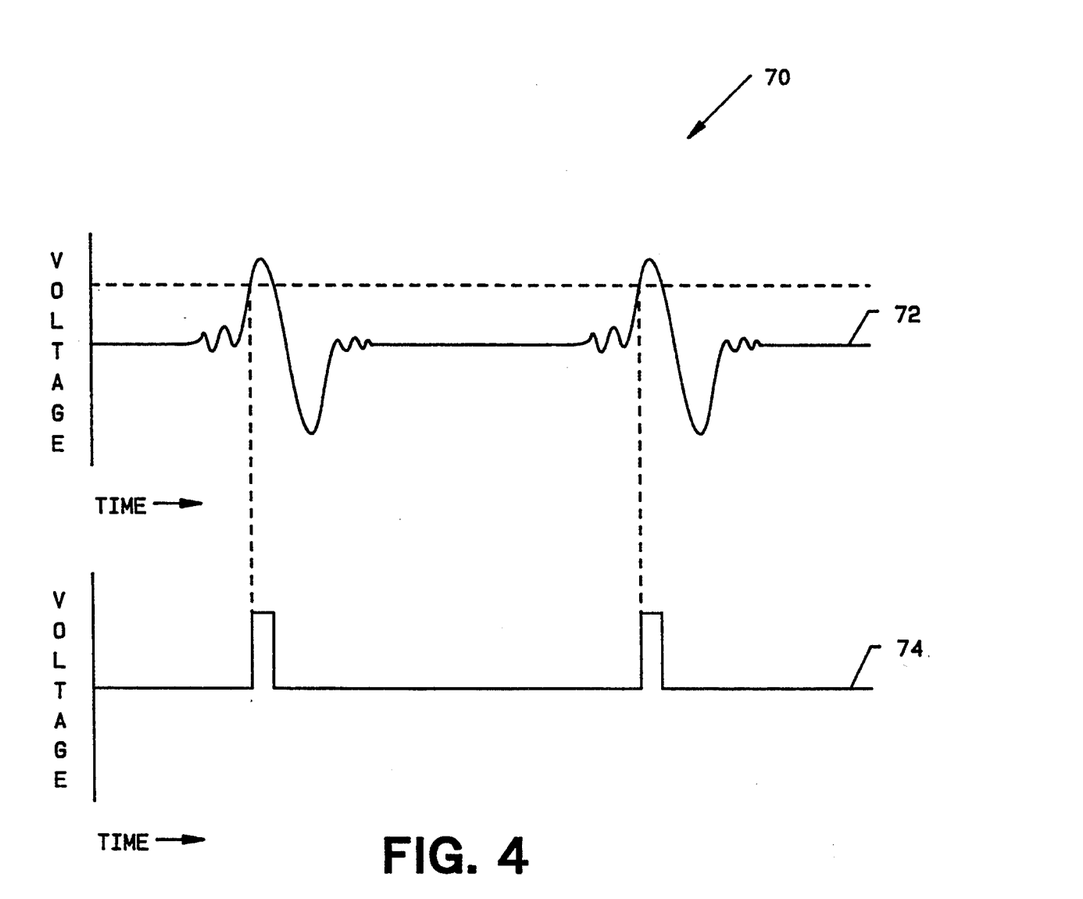
FIG. 4 presents the electrical signal obtained from the pacemaker catheter in FIG. 2, and the standardized digital pulses derived from that signal by sensing the leading edge of each repeated waveform.

A second element of the present invention is reducing the sensed waveform signal to a succession of digital pulses equivalent to one another in height and duration, and differing only in time of occurrence. Each digital pulse can be triggered by some well-defined feature of the waveform, such as a leading edge, a primary maximum, or a trailing edge. Once chosen, however, the triggering feature is constant in the system. The first option, leading-edge triggering, is illustrated in FIG. 4.

Let the balance of this discussion be simplified by assuming that only two electrode pairs are being used. The extension to a larger number of pairs will be evident. Each pair of electrodes will deliver a continuous electrical signal, voltage versus time. Each signal will be converted into a train of uniform digital pulses. The next key element in the present invention, then, is to examine the time relationship of corresponding pulses. In the general case, the corresponding digital pulses will be displaced from one another in time. In principle, then, the balance of the process in the present invention is to examine (a) the magnitude of the temporal displacement, or delay, and (b) the stability of the delay. Modern microelectronics makes it possible to carry out such procedures quickly and inexpensively. Although the design of a system to accomplish this is nontrivial, the principles involved are straightforward.

Figure 5:
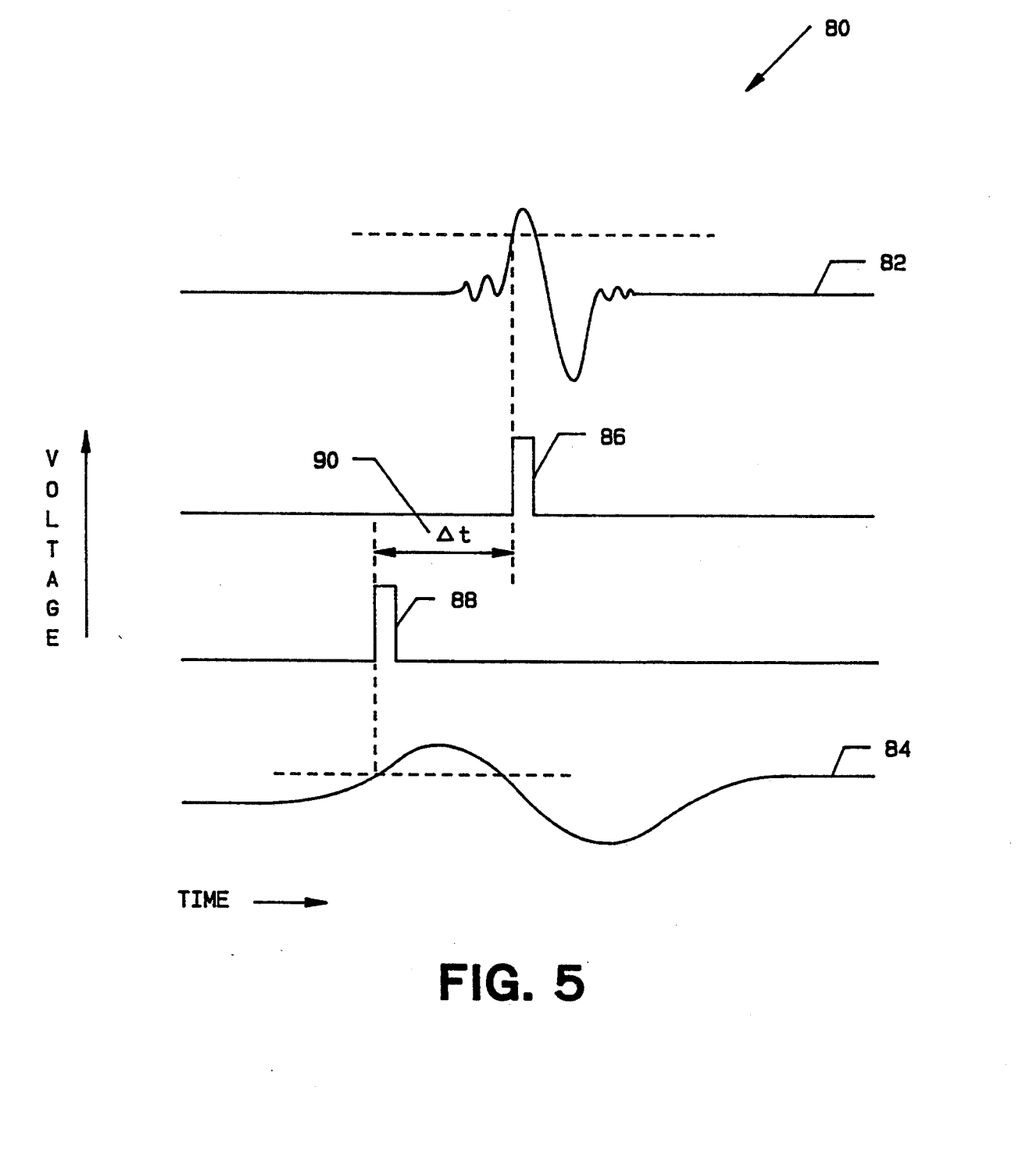
FIG. 5 presents for the normal heart, the local signal from the pacemaker catheter in FIG. 2 and the global signal derived from the epicardial-patch electrodes in FIG. 2.

At this point it is helpful to discuss some electrode options and the kinds of waveforms they typically deliver. Electrodes such as those at the end of a pacing lead can be described as a local or near-field arrangement. They sense the local passage of an activation wavefront, and since the electrodes are about one centimeter apart, the resulting signal is of fairly short duration. By contrast, one can observe far-field or "global" signals by employing electrodes that are (a) more widely spaced, or (b) larger. In the global case, more averaging takes place, and the waveform typically has both a lower amplitude and an expanded duration, such as waveform illustrated in FIG. 5. The reason is that the far-field electrodes observe and average signals coming from a larger portion of the heart. As a result of this relationship between near-field and far-field signals, one can be assured that a digital signal triggered by the leading edge of the latter signal will usually lead that triggered by the leading edge of the local or near-field signal. This is also illustrated in FIG. 5, with the amount of the delay being labeled $\Delta t$. That is, activation anywhere in a large region of the heart will be sensed by the global electrodes, with a high probability of commencing before the local signal is sensed. Thus, in these circumstances, the pulse train derived from the global electrodes will be fed into the delay line.

Figure 2:
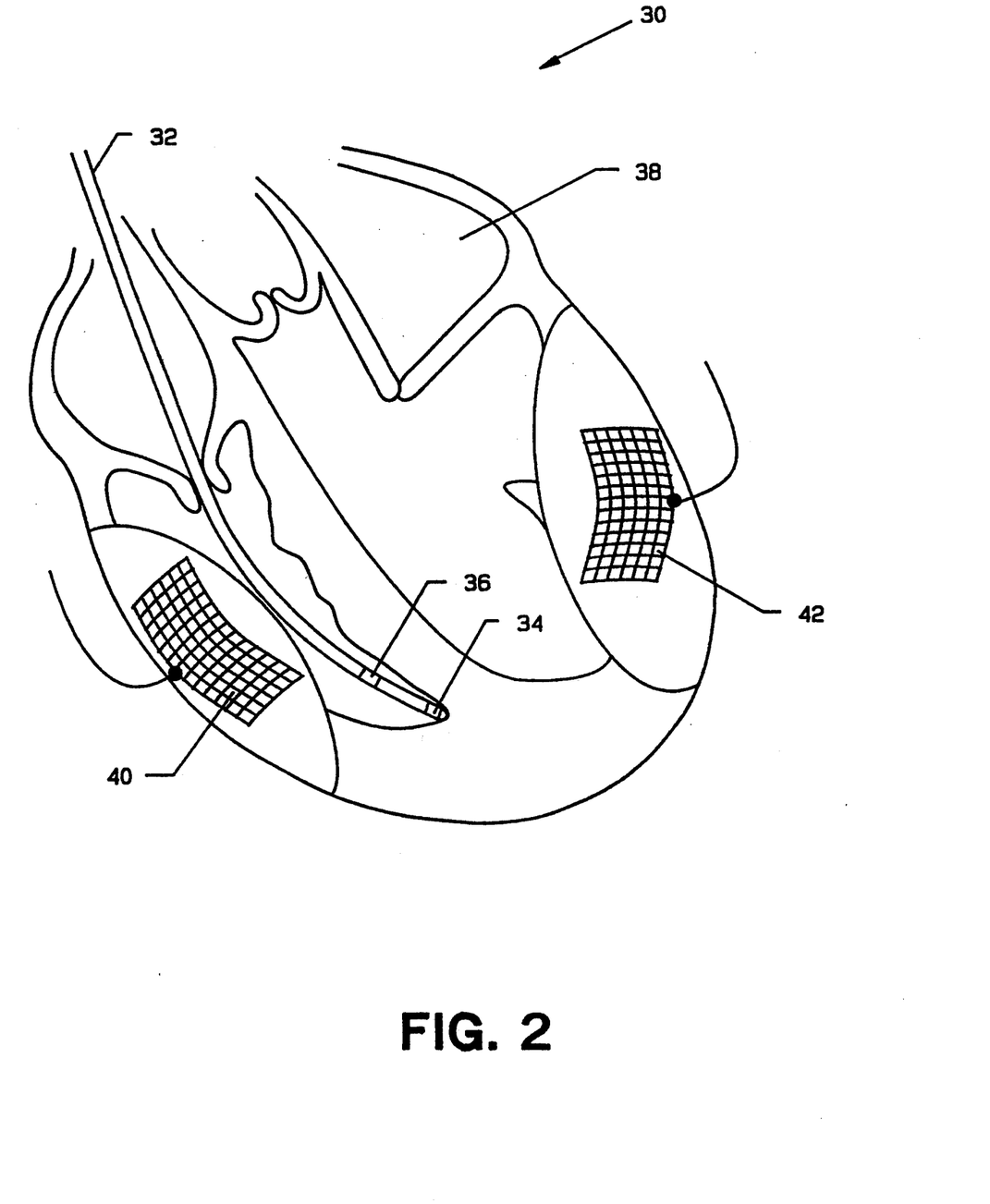
FIG. 2 illustrates schematically the heart with a pacemaker probe in place, and also two epicardial-patch electrodes in place.

In a preferred embodiment of the present invention, a near-field signal will usually be taken from the tip and ring electrodes 14 and 16 of the pacing lead, in FIG. 1 or 34 and 36 in FIG. 2. A far-field signal will be derived from the defibrillation electrodes, such as 18 and 20 or 18 and 24 in FIG. 1 and 40 and 42 in FIG. 2. In one case the defibrillation electrodes are epicardial patches, such as 40 and 42 in FIG. 2. In another case they will be a coil such as coil 18 in FIG. 1, and the housing of a pectorally implanted defibrillator-cardioverter module.

The fact that the delay between the near-field and the far-field signals increases in the condition of monomorphic ventricular tachycardia is helpful in distinguishing among the several tachycardias. [A. J. Camm, et al., "Tachycardia Recognition by Implantable Electronic Devices" PACE, Vol. 10, Sep.–Oct., 1987] It has also been observed for the MVT condition that an increase in delay occurs between two near-field signals taken from separate sites in the heart. [A. D. Mercando and S. Furman, "Measurement of the Differences in Timing and Sequence Between Two Ventricular Electrodes as a means of Tachycardia Differentiation," PACE, Vol. 9, p. 1069, 1986.]

Figure 6:
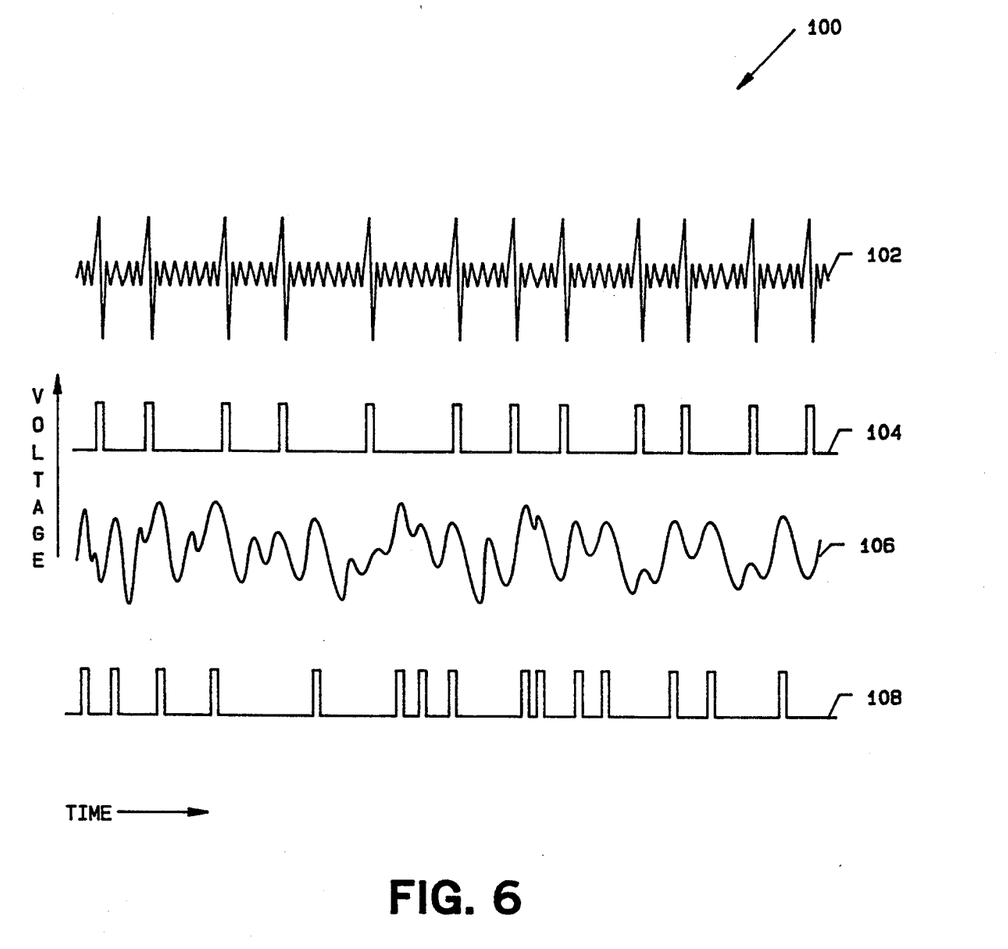
FIG. 6 presents for the fibrillating heart, the local signal derived from the pacemaker catheter of FIG. 2 and the standardized pulses derived from its leading edges, as well as the global signal derived from the epicardial-patch electrodes in FIG. 2 and the standardized pulses derived from its leading edges.

In the case of one preferred embodiment, a pulse train is triggered by the leading edges of signals from far-field defibrillating electrodes, and a delayed pulse train is triggered by the leading edges of signals from the near-field pacing electrodes. Our best information is that the time shift is stable and is smaller than 20 milliseconds for (1) the cases of normal sinus rhythm, sinus tachycardia, and other supraventricular tachycardias. For (2), the case of monomorphic ventricular tachycardia, the time shift is greater than 20 milliseconds, and is still stable. But in (3), the case of ventricular fibrillation, the time shift, if it can be observed, is fleeting and variable, which is to say, unstable, as is illustrated in FIG. 6. Thus, the three-way identification of conditions that require fundamentally different treatment protocols can be established.

A significant variation on the embodiments described above does all of the signal processing with the standardized pulses. In this embodiment a clock is employed, one having a period small compared to that of the heart. Note that a 1-millisecond or 0.1-millisecond clock period meets this description, even though such a period is long by today's standards of digital signal processing. Each standardized pulse is then assigned to the nearest clock period. An advantage of processing the pulse train in lieu of processing the signal coming directly from the heart is that shift registers can be used as delay lines, a precise and economical technique, or microprocessor can be used. Then, if desired, a logical AND gate can be used to establish the coincidence of pulses from two channels.

One significant aspect and feature of the present invention is the reduction of cardiac electrical signals to standardized digital-pulse form so that pulse timing (time of occurrence) is the only remaining information in the signal.

Another significant aspect and feature of the present invention is the comparing of the occurrence times of two or more standardized signals emanating from two or more locations on the heart muscle.

Still another significant aspect and feature of the present invention is observing the occurrence rate of the coincidence of pulses from two or more different channels as a fraction of pulse rate in a single channel.

Yet a further significant aspect and feature of the present invention is observing the delay between corresponding pulses in standardized digital-pulse trains derived from two or more different pairs of electrodes.

Still another significant aspect and feature of the present invention is observing whether the delay exceeds or does not exceed 20 milliseconds.

Another significant aspect and feature of the present invention is doing the bulk of the necessary signal processing with the standardized pulses derived from the signals supplied by the heart.

A further significant aspect and feature of the present invention is using two pacing electrodes and two independent defibrillation electrodes to provide two independent electrical signals, where all these four electrodes are associated with a single pacemaker-defibrillator catheter.

Still another significant aspect and feature of the present invention is using three such electrodes, with one serving in common, to provide two independent electrical signals, where all these electrodes are associated with a single pacemaker-defibrillator catheter.

A further significant aspect and feature of the present invention is using two pacing electrodes and two independent epicardial-patch defibrillation electrodes to provide two independent electrical signals.

Still another significant aspect and feature of the present invention is using three such electrodes, with one serving in common, to provide two independent electrical signals.

Yet another significant aspect and feature of the present invention is using one or more epicardial-patch electrodes in an assembly providing two or more channels of information from the heart.

An even further significant aspect and feature of the present invention is using one or more subcutaneous-patch electrodes in the assembly providing two or more channels of information from the heart.

Still another significant aspect and feature of the present invention is using one or more endocardial-coil electrodes in the assembly providing two or more channels of information from the heart.

Having thus described the embodiments of the present invention, it is a principal object hereof to provide a clearer and more reliable indication of the onset of ventricular fibrillation than has been available in the prior art.

One object of the present invention is to distinguish reliably among ventricular fibrillation, monomorphic ventricular tachycardia, and a set of conditions comprising normal sinus rhythm, sinus tachycardia, and other supraventricular tachycardias.

Another object of the present invention is to compare electrical signals taken from the heart by means of two or more electrode pairs that may or may not be independent.

Yet another object of the present invention is to make diagnostic comparisons in terms of standardized digital pulses derived from electrical signals taken from the heart by means of electrode systems.

Still another object of the present invention is to observe standardized-pulse correlations.

Another object of the present invention is to observe the presence or absence of any systematic delay between corresponding pulses in trains of standardized pulses.

Yet another object of the present invention is to use electrodes for multiple purposes, including pacing, sensing, cardioversion, and defibrillation.

A further object of the present invention is to observe the occurrence rate of the coincidence of pulses from two or more different channels as a fraction of pulse rate in a single channel.

Still another object of the present invention is to employ digital signal-processing techniques for convenience and economy in providing variable delays and coincidence determinations.

BRIEF DESCRIPTION OF THE DRAWINGS

Other objects of the present invention and many of the attendant advantages of the present invention will be readily appreciated as the same becomes better understood by reference to the following detailed description when considered in connection with the accompanying drawings, in which like reference numerals designate like parts throughout the figures thereof and wherein.

DESCRIPTION OF THE PREFERRED EMBODIMENTS

FIG. 1 illustrates various electrode options 10, comprising a conventional pacemaker-defibrillator catheter 12 carrying bipolar pacing electrodes 14 and 16, and two defibrillating electrodes 18 and 20, with electrode 18 in its normal position within the right ventricle 19, and electrode 20 within the right atrium 21, of the heart 22, and with a subcutaneous-patch electrode 24 also present; the catheter 12 can also be positioned with at least one electrode in the superior vena cava 26, as well as in the nearby coronary sinus that cannot readily be represented in this particular cross-sectional diagram of the heart 22.

FIG. 2 illustrates prior art electrode options 30, comprising a conventional pacemaker lead 32 carrying bipolar pacing electrodes 34 and 36 in their normal positions within the heart 38, and also two epicardial-patch defibrillating electrodes 40 and 42 attached to the heart 38 in normal fashion.

Figure 3:
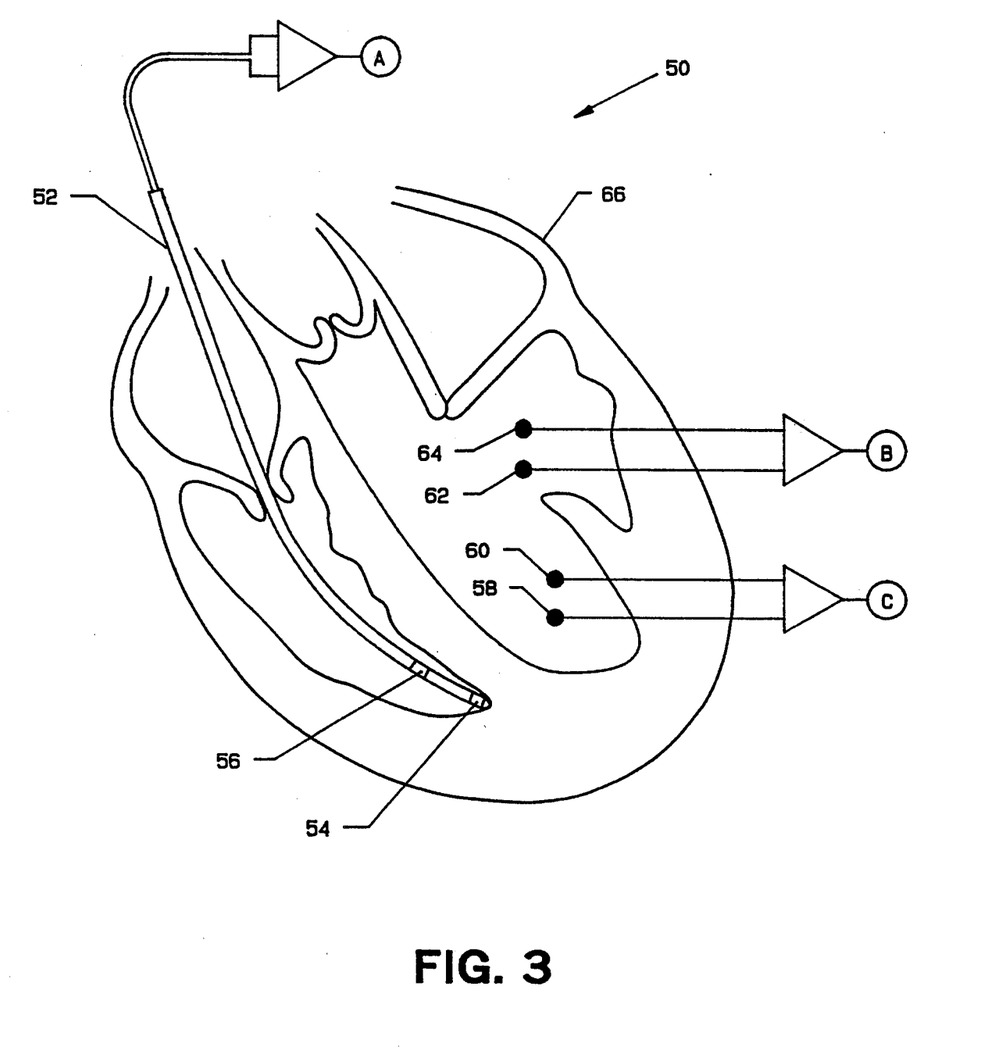
FIG. 3 illustrates schematically the heart with pacing electrodes on a catheter in place, and also two additional pairs of epicardial-pace/sense electrodes in place.

FIG. 3 illustrates schematically other electrode configurations 50 comprising a conventional pacing catheter 52 carrying bipolar pacing electrodes 54 and 56 in combination with a first additional pair of epicardial-patch electrodes 58 and 60, and a second additional pair of epicardial-patch electrodes 62 and 64, these several electrodes positioned in and on the heart 66. Signals are sensed at conductor pair A for electrodes 54 and 56, at pair B for epicardial electrodes 62 and 64, and at pair C for epicardial electrodes 58 and 60.

FIG. 4 presents electrical signals 70, voltage versus time, of the present invention, comprising the signal 72 observed from the normal heart with pacing electrodes, the standardized-pulse signal 74 derived from it by leading-edge sensing.

FIG. 5 presents the electrical signals 80, voltage versus time, from the normal heart, comprising the near-field signal 82 observed with the pacing electrodes 34 and 36 of FIG. 2, and the far-field signal 84 observed with the epicardial-patch defibrillating electrodes 40 and 42 of FIG. 2, as well as the standardized digital pulse 86 derived from the leading edge of the waveform in the near-field signal 82, and the standardized digital pulse 88 derived from the leading edge of the waveform of the far-field signal 84, and finally the time delay 90 between the standardized digital pulses 86 and 88.

FIG. 6 presents the electrical signals 100, voltage versus time, from the fibrillating heart, comprising the near-field signal 102 observed with the pacing electrodes 34 and 36 of FIG. 2, and the standardized-digital-pulse train 104 derived from the leading edges of the waveforms in the near-field signal 102, as well as the far-field signal 106 observed with the epicardial-patch electrodes 40 and 42 of FIG. 2, and the standardized-digital-pulse train 108 derived from the leading edges of the waveforms of the far-field signal 106, showing the lack of correlation between the pulses of the standardized-digital-pulse train 104 and those of the standardized-digital-pulse train 108.

Figure 7:
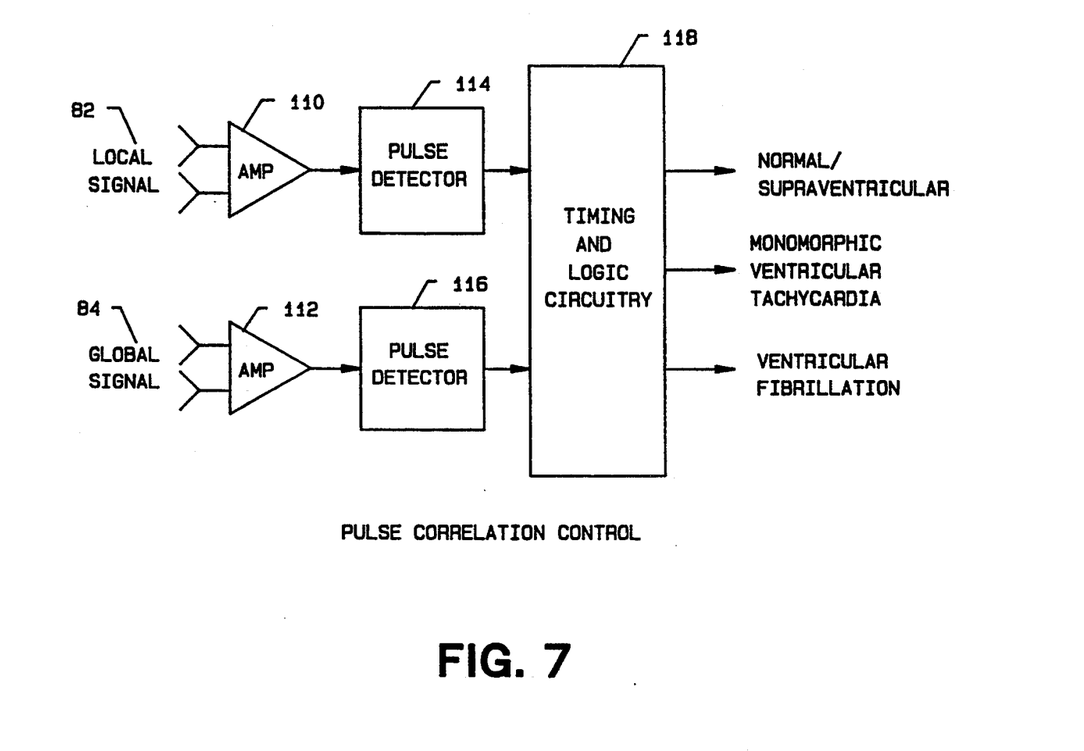
FIG. 7 illustrates a block diagram for pulse correlation control.

FIG. 7 illustrates a block diagram 109 for pulse correlation control where all numerals correspond to those elements previously described. The local signal 82 and global signal 84 each have independent amplifiers 110 and 112. The amplifiers 110 and 112 increase the signal amplitudes from as low as 100 microvolt to above 1 volt. Each amplified signal is then fed into its respective pulse detector 114 and 116 which issues a digital pulse when a predetermined feature, such as a leading edge, of a cardiac signal, is detected. Timing and logic circuitry 118 measures the relative timing between the two pulse indications and declares the heart to be in a particular one of the several conditions comprising normal sinus rhythm, supraventricular tachycardia, monomorphic ventricular tachycardia, and ventricular fibrillation.

Figure 8:
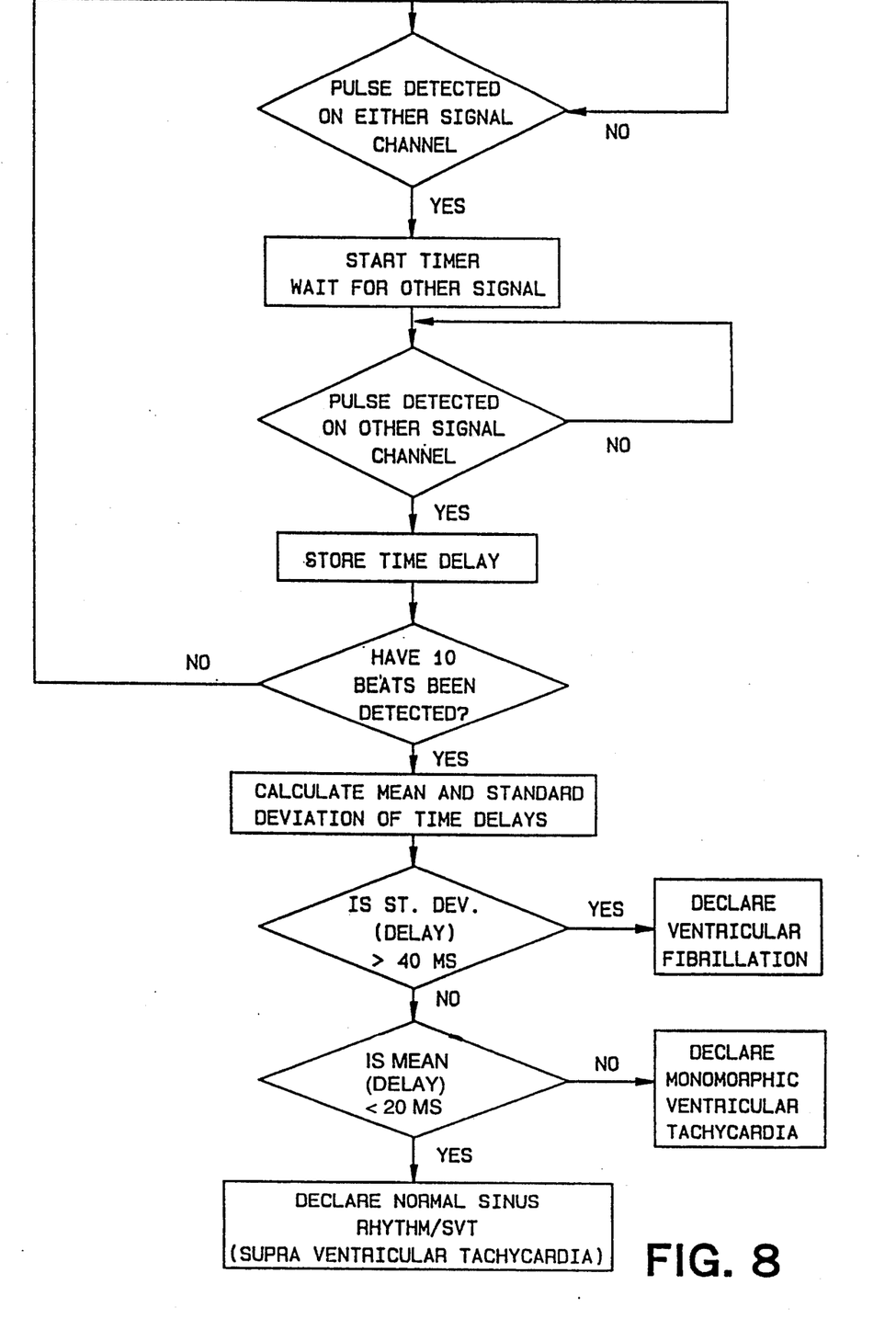
FIG. 8 illustrates a flow chart for the timing and logic circuitry.

FIG. 8 illustrates a flow chart 120 for the timing and logic circuitry 118 where all numerals correspond to those elements previously described.

MODE OF OPERATION

Substantial variety in the choice of electrodes is available for the purpose of creating two or more channels of information on the electrical activity of the heart, which is one essence of the present invention. For example, conventional pacing electrodes on a standard pacemaker catheter can constitute one channel. Conventional defibrillator electrodes on the same or a different catheter can constitute a second channel. Two channels can also be achieved by using three electrodes, by letting one of the foregoing electrodes be common to two or more channels. One or two epicardial-patch electrodes can be used to realize an additional channel. The same is true of one or two endocardial-coils and one or two subcutaneous-patch electrodes. The housing of the defibrillator-cardioverter module can also be used as one of the far-field electrodes.

The present invention aims to provide a sensitive, prompt, and accurate indication of the onset of ventricular fibrillation, and of monomorphic ventricular tachycardia, being triggered to apply these methods by any departure from normal sinus rhythm in the usual range, 60 to 120 per minute. It exploits the most prominent feature of the fibrillation condition, the absence of coordinated or synchronous contraction by the various elements of the heart muscle. The invention observes electrical voltage-versus-time signals from two or more locations on or in the heart. By well-known signal-processing techniques, these signals are reduced to pulses of standardized height and duration, each derived from a prominent feature of the waveform for each heart period, such as its leading edge or its primary maximum, in the process eliminating the irrelevant information in the waveform, but retaining the feature that is most relevant in the present context, namely, its precise time of occurrence. The invention then uses further standard electronic techniques, especially counters, for the purpose of determining the amount of delay between the sets of standardized pulses. Determining the amount of delay permits a distinction between monomorphic ventricular tachycardia, for which a low-energy shock (or cardioversion) is in order, and other conditions of tachycardia for which a shock is unnecessary or unhelpful. Thus, the present invention is able to trigger a cardioversion-discharge decision more reliably than has been possible in the prior art.

The assessment of pulse coincidence, or simultaneity, is also a matter of standard electronic technique. And it is a further straightforward matter of signal analysis to determine coincidence rate as a fraction of total pulse rate. In the normal heart, this fraction approaches unity (100%), while in the fibrillating heart, it can be expected to be much lower. Thus, the present invention is able to trigger a defibrillating-discharge decision much more reliably than has been possible in the prior art.

Various modifications can be made to the present invention without departing from the apparent scope hereof.

We claim:

1. (Twice Amended) An improved fibrillation and tachycardia detection system for a cardioversion-defibrillation system including means for detecting whether a patient's heart is in a normal cardiac rhythm or an abnormal cardiac rhythm and, in response to detection of an abnormal cardiac rhythm, means for automatically delivering an electrical countershock therapy of greater than about 1.0 joules of electrical energy to treat the abnormal cardiac rhythm, the improvement comprising:

local detection means for sensing a local electrical signal representing cardiac activity in one of a plurality of local areas of the patient's heart, each local area having a local electrical signal;

global detection means for sensing a global electrical signal representing cardiac activity in a global area of the patient's heart, the global area including the plurality of the local areas such that the global electrical signal represents an electrical average of the local electrical signals of the plurality of local areas;

means for successively measuring a delay value between a first time when the local electrical signal meets a predetermined trigger criteria and a second time when the global electrical signal meets the predetermined trigger criteria;

means for storing and comparing a series of the delay values to detect whether the patient's heart is in the abnormal cardiac rhythm and should be treated by the cardioversion defibrillation system or whether the patient's heart is in the normal cardiac rhythm and should not be treated by the cardioversion defibrillation system.

2. The detection system of claim 1 wherein the global detection means comprises at least one far-field electrode.

3. The detection system of claim 2 wherein the far-field electrode is an epicardial-patch electrode.

4. The detection system of claim 2 wherein the far-field electrode is a subcutaneous-patch electrode.

5. The detection system of claim 2 wherein the far-field electrode is an implanted housing which houses the cardioversion defibrillation system as an implantable device.

6. The detection system of claim 1 wherein the means for storing and comparing comprises:
   means for storing the series of delay values;
   means for determining a mean for the series of the delay values;
   means for determining a standard deviation for the series of the delay values;
   means for indicating detection of a ventricular fibrillation if the standard deviation is greater than a first predetermined value, the ventricular fibrillation to be treated by delivery of a defibrillation countershock therapy; and
   means for indicating detection of a monomorphic tachycardia if the mean is greater than a second predetermined value, the monomorphic tachycardia to be treated by delivery of a cardioversion countershock therapy.

7. The detection system of claim 1 wherein the means for successively measuring comprises:
   first pulse detector means for generating a first digital pulse when the local electrical signal meets the predetermined trigger criteria;
   second pulse detector means for generating a second digital pulse when the global electrical signal meets the predetermined trigger criteria; and
   means for measuring a time period between the first and second digital pulse to generate the delay value.

8. The detection system of claim 7 wherein the means for measuring the time period comprises a clocked shift register.

9. The detection system of claim 7 wherein the means for measuring the time period comprises a clocked counter.

10. The detection system of claim 7 wherein the means for storing and comparing comprises:
    means for delaying the first digital pulse by a predetermined amount such that a delayed first digital pulse and the second digital pulse are coincident when the patient's heart is in the normal cardiac rhythm;
    means for sensing the coincidence over the series of the delays between the delayed first digital pulses and the second digital pulses to detect whether the patient's heart is in a ventricular fibrillation; and
    means for determining if an average of the time periods over the series of delays is greater than a predetermined value to detect whether the patient's heart is in a monomorphic tachycardia.

11. The detection system of claim 1 wherein the local detection means comprises a pair of point electrodes spaced apart from one another by less than about 1 centimeter and the global detection means comprises a pair of point electrodes spaced apart from one another by greater than about 1 centimeter.

12. A method of fibrillation and tachycardia detection for a cardioversion-defibrillation device capable of automatically delivering an electrical countershock therapy of greater than 1.0 joules of electrical energy to treat a patient's heart in response to detection of an abnormal cardiac rhythm, the method comprising the device-implemented steps of:
    (a) providing a local electrical signal representing cardiac activity in one of a plurality of local areas of the patient's heart, each local area having a local electrical signal;
    (b) providing a global electrical signal representing cardiac activity in a global area of the patient's heart including the plurality of local areas such that the global electrical signal represents an electrical average of the local electrical signals of the plurality of local areas;
    (c) detecting when either the local electrical signal or the global electrical signal meet a predetermined trigger condition and starting a delay timer;
    (d) detecting when the one of either the local electrical signal of the global electrical signal not detected in step (c) meets the predetermined trigger condition and stopping the delay timer;
    (e) storing a delay value from the delay timer for each of a series of trigger conditions;
    (f) comparing the series of delay values to detect whether the patient's heart is in the abnormal cardiac rhythm and should be treated by the cardioversion defibrillation system or whether the patient's heart is in the normal cardiac rhythm and should not be treated by the cardioversion defibrillation system.

13. The method of claim 12 wherein step (f) comprises:
    (f1) determining a mean for the series of the delay values;
    (f2) determining a standard deviation for the series of the delay values;
    (f3) indicating detection of a ventricular fibrillation if the standard deviation is greater than a first predetermined value, the ventricular fibrillation to be treated by delivery of a defibrillation countershock therapy; and
    (f4) indicating detection of a monomorphic tachycardia if the mean is greater than a second predetermined value, the monomorphic tachycardia to be treated by delivery of a cardioversion countershock therapy.

* * * * *